(12) United States Patent
Sumiyoshi

(10) Patent No.: US 8,735,809 B2
(45) Date of Patent: May 27, 2014

(54) CHROMATOGRAPH MASS SPECTROMETER

(71) Applicant: Shimadzu Corporation, Kyoto (JP)

(72) Inventor: Takashi Sumiyoshi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 25 days.

(21) Appl. No.: 13/890,558

(22) Filed: May 9, 2013

(65) Prior Publication Data

US 2013/0240727 A1    Sep. 19, 2013

(30) Foreign Application Priority Data

Dec. 22, 2010  (JP) ................... 2010-285555

(51) Int. Cl.
*B01D 59/44*    (2006.01)

(52) U.S. Cl.
USPC ............ 250/282; 250/281; 250/287; 250/288

(58) Field of Classification Search
USPC .................... 250/281, 282, 287, 288
See application file for complete search history.

(56) References Cited

U.S. PATENT DOCUMENTS

| | | | | |
|---|---|---|---|---|
| 4,507,555 A * | 3/1985 | Chang | | 250/281 |
| 5,367,162 A * | 11/1994 | Holland et al. | | 250/287 |
| 5,602,755 A * | 2/1997 | Ashe et al. | | 702/30 |
| 7,269,994 B2 * | 9/2007 | Umemura | | 73/23.37 |
| 7,619,212 B2 * | 11/2009 | Miyagawa | | 250/282 |
| 7,759,130 B2 * | 7/2010 | Oda et al. | | 436/173 |
| 7,799,576 B2 * | 9/2010 | Pappin et al. | | 436/173 |
| 7,982,180 B2 * | 7/2011 | Shilov et al. | | 250/281 |
| 8,168,942 B2 * | 5/2012 | Sumiyoshi | | 250/281 |
| 2003/0213908 A1 * | 11/2003 | Umemura | | 250/292 |
| 2005/0252275 A1 * | 11/2005 | Kita et al. | | 73/23.34 |
| 2007/0218505 A1 * | 9/2007 | Kearney | | 435/7.1 |
| 2009/0008542 A1 * | 1/2009 | Sumiyoshi | | 250/281 |
| 2009/0065686 A1 * | 3/2009 | Shilov et al. | | 250/252.1 |
| 2009/0283673 A1 * | 11/2009 | Shilov et al. | | 250/282 |
| 2013/0240727 A1 * | 9/2013 | Sumiyoshi | | 250/288 |

FOREIGN PATENT DOCUMENTS

JP    2003-172726 A    6/2003

* cited by examiner

*Primary Examiner* — David A Vanore
(74) *Attorney, Agent, or Firm* — Sughrue Mion, PLLC

(57) ABSTRACT

After an analysis condition table for measuring each compound is automatically generated in accordance with a compound table, the loop time is calculated for each measurement section for which the overlapping of measurement events differs. If the loop time exceeds a specified value in a given measurement section of a given compound, the event with the earliest end time and the event with the latest start time are extracted from among the overlapping measurement events, and the intermediate time between the end time and the start time is found to adjust the length of each measurement event. By repeating this process, a parameter in the analysis condition table is corrected so that the loop time becomes equal to or less than the specified value.

3 Claims, 6 Drawing Sheets

COMPOUND TABLE

Figure 1:
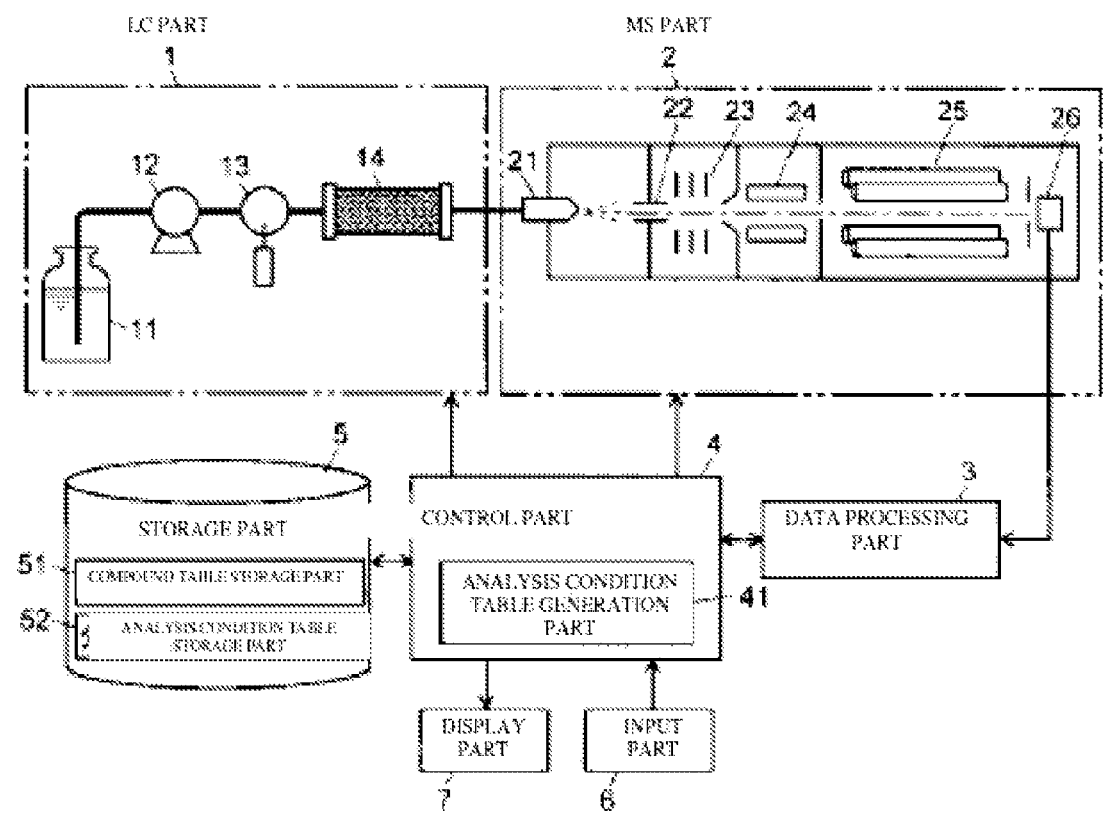

| No | COMPOUND NAME | QUANTITATIVE ION m/z | CONFIRMATION ION m/z | PREDICTED RETENTION TIME (min) | MEASUREMENT TIME RANGE (min) | REQUIRED LOOP TIME (msec) |
|---|---|---|---|---|---|---|
| 1 | A | 100 | 200 | 10.000 | ±1 | 200 |
| 2 | B | 300 | 400 | 10.400 | ±1 | 200 |
| 3 | C | 500 | 600 | 11.200 | ±1 | 200 |
| 4 | D | 700 | 800 | 12.000 | ±1 | 200 |
| 5 | E | 900 | 1000 | 12.400 | ±1 | 200 |

FIG. 3

(a)

| SECTION | LOOP TIME (msec) |
|---|---|
| 1 | 100 |
| 2 | 200 |
| 3 | 300 |
| 4 | 300 |
| 5 | 300 |
| 6 | 200 |
| 7 | 100 |

(b)

| SECTION | LOOP TIME (msec) |
|---|---|
| 1 | 100 |
| 2 | 200 |
| 3 | 200 |
| 4 | 300 |
| 5 | 300 |
| 6 | 200 |
| 7 | 100 |

(c)

| SECTION | LOOP TIME (msec) |
|---|---|
| 1 | 100 |
| 2 | 200 |
| 3 | 200 |
| 4 | 200 |
| 5 | 200 |
| 6 | 100 |

FIG. 4

ANALYSIS CONDITION TABLE

| MEASUREMENT EVENT No. | MEASURE- MENT MODE | COMPOUND NAME | MEASUREMENT ION m/z | MEASUREMENT START TIME (min) | MEASUREMENT END TIME (min) | EVENT TIME (msec) |
|---|---|---|---|---|---|---|
| 1 | SIM | A | 100, 200 | 9.000 | 11.000 | 100 |
| 2 | SIM | B | 300, 400 | 9.400 | 11.200 | 100 |
| 3 | SIM | C | 500, 600 | 10.600 | 11.800 | 100 |
| 4 | SIM | D | 700, 800 | 11.200 | 13.000 | 100 |
| 5 | SIM | E | 900, 1000 | 11.800 | 13.400 | 100 |

COMPOUND TABLE

| No | COMPOUND NAME | QUANTITATIVE ION m/z | CONFIRMATION ION m/z | PREDICTED RETENTION TIME (min) | MEASUREMENT TIME RANGE (min) |
|---|---|---|---|---|---|
| 1 | A | 100 | 200 | 10.000 | ±1 |
| 2 | B | 300 | 400 | 10.400 | ±1 |
| 3 | C | 500 | 600 | 11.200 | ±1 |
| 4 | D | 700 | 800 | 12.000 | ±1 |
| 5 | E | 900 | 1000 | 12.400 | ±1 |

FIG. 9

ANALYSIS CONDITION TABLE

| MEASUREMENT EVENT No. | MEASUREMENT MODE | COMPOUND NAME | MEASUREMENT ION m/z | MEASUREMENT START TIME (min) | MEASUREMENT END TIME (min) | EVENT TIME (msec) |
|---|---|---|---|---|---|---|
| 1 | SIM | A | 100,200 | 9.000 | 11.000 | 100 |
| 2 | SIM | B | 300,400 | 9.400 | 11.400 | 100 |
| 3 | SIM | C | 500,600 | 10.200 | 12.200 | 100 |
| 4 | SIM | D | 700,800 | 11.000 | 13.000 | 100 |
| 5 | SIM | E | 900,1000 | 11.400 | 13.400 | 100 |

FIG. 10

| SECTION | LOOP TIME (msec) |
|---|---|
| 1 | 100 |
| 2 | 200 |
| 3 | 300 |
| 4 | 300 |
| 5 | 300 |
| 6 | 200 |
| 7 | 100 |

FIG. 11

CHROMATOGRAPH MASS SPECTROMETER

TECHNICAL FIELD

The present invention relates to a chromatograph mass spectrometer combining a chromatograph and a mass spectrometer such as a gas chromatograph mass spectrometer (GC/MS) or a liquid chromatograph mass spectrometer (LC/MS). More specifically, the present invention relates to a chromatograph mass spectrometer which performs measurements such as selected ion monitoring (SIM), selection reaction monitoring (SRM), or multiple reaction monitoring (MRM) with respect to known components in a mass spectrometer.

BACKGROUND ART

Chromatograph mass spectrometers combining a chromatograph such as a gas chromatograph (GC) or a liquid chromatograph (LC) and a mass spectrometer such as a quadrupole mass spectrometer are widely used to perform qualitative or quantitative analyses of various components contained in a sample. When performing qualitative analyses of known components using a chromatograph mass spectrometer, an SIM measurement method is typically used, whereby only ions having one or a plurality of specific mass-to-charge ratios designated in advance are selectively and repeatedly detected.

That is, in a chromatograph mass spectrometer, an analysis is executed by setting the mass-to-charge ratio of a known target component so that it is subjected to SIM measurements, whereby the elapsed time of the intensity of ions having this mass-to-charge ratio is obtained, so this can be plotted to find an extracted ion chromatogram (also called a mass chromatogram) with respect to the target component. In order to perform a qualitative analysis, peaks appearing in the vicinity of the retention times of known components are detected in this extracted ion chromatogram, and the peak areas are found and reflected in a predetermined calibration curve to reduce the areas to the content of the target component.

In order to perform a qualitative analysis using SIM measurements as described above, it is necessary to set analysis conditions such as the mass-to-charge ratios to be measured prior to analysis. For example, the chromatograph mass spectrometer described in Patent Literature 1 is provided with a function which, when an analyst creates a compound table describing information about compounds to be measured, automatically creates an analysis condition table based on the information described in the table. Such an analysis condition table creation function in a conventional chromatograph mass spectrometer will be described using a specific example.

FIG. 9 is an example of a compound table. As shown in the figure, the compound table includes information such as the compound name, the mass-to-charge ratio of a quantitative ion, the mass-to-charge ratio of a confirmation ion, the predicted retention time, and the measurement time range for each compound. A qualitative ion is an ion which best characterizes the compound. A confirmation ion is an ion having a mass-to-charge ratio differing from that of the qualitative ion which characterizes the compound. This confirmation ion is used to confirm that the chromatogram peak of the qualitative ion is derived from the target compound using the relative ratio of the signal intensity of the confirmation ion peak and the signal intensity of the qualitative ion peak in the mass spectrum. The predicted retention time is the predicted value of the time of elution from a column in the chromatograph. The measurement time range is a parameter for designating the time range for which the compound should be measured around the predicted retention time.

FIG. 10 is an example of an analysis condition table created automatically with respect to the compound table described above. In the analysis condition table, the analysis conditions for one compound are summarized in one line as a "measurement event." That is, each measurement event includes the compound name as well as the measurement mode (selection of the SIM measurement mode or the scan measurement mode), the mass-to-charge ratios of measurement ions, the measurement start time, the measurement end time, and the event time. The mass-to-charge ratios of the qualitative ion and the confirmation ion of the compound to be measured are set for the mass-to-charge ratios of the measurement ions. A time determined by tracing back by the measurement time range from the predicted retention time of the compound to be measured is set for the measurement start time. The time after the measurement time range has elapsed from the predicted retention time of the compound to be measured is set for the measurement end time. The event time is the unit time of the repetition of the measurement event, and this is set to a value predetermined by the analyst.

In FIG. 10, the measurement event #1 (the measurement event number is expressed by "#") for measuring compound A, for example, is in the SIM measurement mode, which means that two mass-to-charge ratios of m/z=100 and m/z=200 are repeatedly measured in 100 msec units for 2 minutes from the 9.0 min mark to the 11.0 min mark. As a result of executing an analysis in accordance with the analysis condition table shown in FIG. 10, an extracted ion chromatogram such as that shown in FIG. 6, for example, is obtained. However, although only one chromatogram is shown for one measurement event here, the number of chromatograms created corresponds to the number of measurement ions (in this example, two for each compound).

Figures 5, 6:
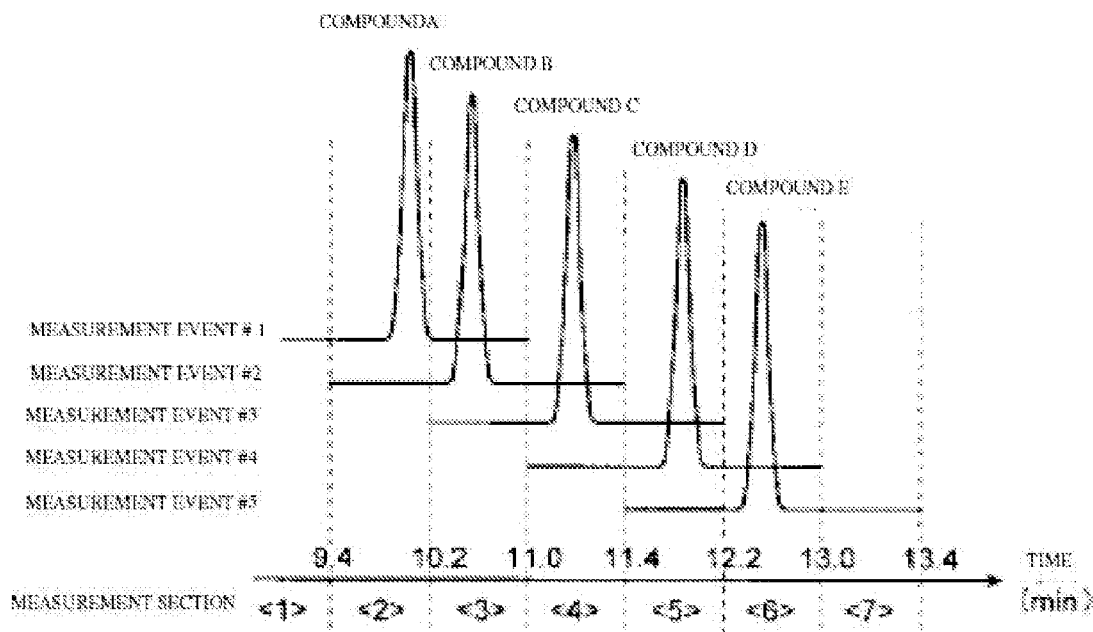

As can be seen from FIGS. 6 and 10, the three measurement periods of the measurement events #1, #2, and #3 overlap during the 0.8 minutes from the 10.2 min mark to the 11.0 min mark. Since a plurality of measurements with overlapping measurement periods will be performed sequentially in a time-sharing manner, the measurement point time interval for one compound becomes wider as the number of overlapping measurement periods increases. For example, since three measurement events overlap in the period from the 10.2 min mark to the 11.0 min mark, an event time of 100 msec×3=300 msec for one measurement becomes the measurement point time interval. Here, the measurement point time interval is called the loop time. In the example shown in FIG. 6, the loop times in the measurement sections <1> to <7> are as shown in FIG. 11.

When the predicted retention times of a plurality of compounds to be measured are in close proximity to one another, the overlapping of different measurement events in time increases, so the loop times increase. When the loop time increases in a given measurement section, the measurement point time interval opens in that measurement section, which reduces the number of data points constituting the chromatogram peak and reduces the precision or reproducibility of the peak area. As a result, the precision or reproducibility of the quantitative analysis is reduced. In order to obtain sufficient peak area reproducibility, at least ten data points are typically necessary for one chromatogram peak, and it is necessary to increase the number of data points further depending on the required quantitative precision or reproducibility. Therefore, the analyst determines the upper limit of the loop time for each compound in accordance with the required quantitative precision or reproducibility and adjusts the parameters of the measurement event so that the loop time determined by the analysis conditions is equal to or less than the upper limit.

Specifically, after an analysis condition table is automatically created based on the compound table as described above, the analyst confirms whether the loop time of each measurement interval is equal to or less than the predetermined upper limit. If the loop time exceeds the upper limit, the analyst adjusts the start time or the end time of the measurement event so that there is no overlapping of measurement events. However, in a conventional chromatograph mass spectrometer, such an assessment of the overlapping of measurement sections or the parameter adjustment of measurement events must be performed manually by the analyst in the analysis condition table or the like, which is a very troublesome and time-consuming operation for the operator. Moreover, there is also a risk of setting parameters erroneously, in which case appropriate quantitative results cannot be obtained.

PRIOR ART LITERATURES (PATENT LITERATURE 1) Japanese Unexamined Patent Application Publication 2003-172726

SUMMARY OF THE INVENTION

The present invention was conceived in order to solve the problems described above, and the purpose of the present invention is to provide a chromatograph mass spectrometer with which an analysis condition table in which parameters values of measurement events are adjusted appropriately can be created without inconveniencing the analyst so that loop times satisfy the desired values as much as possible over all measurement periods.

The present invention, which was conceived in order to solve the problems described above, is a chromatograph mass spectrometer combining a chromatograph for separating compounds in a sample in the time direction and a mass spectrometer for separating and detecting ions derived from the compounds separated by the chromatograph in accordance with the mass-to-charge ratio, wherein the mass spectrometer executes selected ion monitoring (SIM), selection reaction monitoring (SRM), or multiple reaction monitoring (MRM) with respect to one or a plurality of specific mass-to-charge ratios in the vicinity of a chromatogram peak corresponding to a target compound, the chromatogram mass spectrometer comprising:

a) a compound table holding means which stores a compound table containing information indicating, for each compound to be measured, at least the standard predicted retention time, the mass-to-charge ratio characterizing the compound, and the upper limit of the measurement point time interval; and b) an analysis condition table creation means which, in order to perform SIM measurements, SRM measurements, or MRM measurements on compounds listed in the compound table, creates an analysis condition table containing information indicating at least the measurement time range and the mass-to-charge ratios to be measured for each compound to be measured based on the information contained in the compound table;

wherein the analysis condition table creation means includes a correction means which, after the analysis condition table creation means temporarily creates an analysis condition table based on the information contained in the compound table, corrects the analysis condition table by adjusting the start time and the end time of the measurement time range for each compound so that the measurement time interval for each compound falls within the upper limit of the measurement time interval set in the compound table.

In the chromatograph mass spectrometer of the present invention, when the analysis condition table creation means creates an analysis condition table based on the information contained in the compound table, a prescribed measurement time range is secured in the vicinity of the predicted retention time of each compound to find the measurement time range (measurement start time and measurement end time), but this measurement time range may be set for each compound in the compound table or may be set for all of the compounds collectively. In either case, when the analysis condition table is initially created based on the information contained in the compound table, overlapping of the measurement time ranges in time with respect to each compound is not taken into consideration, so the overlapping of the measurement time ranges increases when there are many compounds with similar predicted retention times. As a result, the measurement point time interval widens.

Therefore, in the chromatograph mass spectrometer of the present invention, a correction means contained in the analysis condition table creation means calculates the measurement point time interval (loop time) for each compound in accordance with the created analysis condition table, and when the calculated value exceeds the upper limit, adjusts the start time and the end time of the measurement time range for each compound so that the calculated value falls within the upper limit.

As one specific mode, the correction means may be configured so that, if measurement times for a plurality of specified compounds overlap in time in the analysis condition table so that the measurement point time interval exceeds the upper limit in the overlapping sections, the correction means advances the end time of a first measurement period which ends earliest among the overlapping sections and postpones the start time of a second measurement period which starts latest among the overlapping sections so as to eliminate the overlapping of the first measurement period and the second measurement period in time.

A chromatogram peak should appear earliest in time for a compound for which the first measurement period which ends earliest among the overlapping sections is set, and conversely, a chromatogram peak should appear latest in time for a compound for which the second measurement period which begins latest among the overlapping sections is set. Accordingly, even if the end time of the first measurement period is advanced or the start time of the second measurement period is postponed, the likelihood that the chromatogram peak generation period (period from the starting point to the ending point of the peak) will be curtailed is low. That is, with the processing described above, it is possible to keep the measurement point interval within the upper limit without affecting the acquisition of chromatogram peaks of the compounds to be measured. As a result, it is possible to improve the precision or reproducibility of the chromatogram peak waveform shapes while eliminating troublesome operations to be performed by the analyst.

Further, the correction means may also be configured so as to find the intermediate time between the end time of the first measurement interval and the start time of the second measurement interval, advance the end time of the first measurement interval to the intermediate time, and postpone the start time of the second measurement interval to the intermediate time. As a result, it is possible to reliably eliminate the overlapping of the first and second measurement periods with simple processing.

With the chromatograph mass spectrometer of the present invention, an analysis condition table is automatically corrected so that the measurement point time intervals for all compounds to be measured fall within the required upper limits to the greatest degree possible without the analyst (user) performing troublesome calculations, operations, or processes. As a result, it is possible to obtain the peak waveform shapes of the target components in the extracted ion chromatogram with high precision and reproducibility while reducing the burden on the analyst and preventing the occurrence of mistakes, which makes it possible to improve the precision or reproducibility of quantitative values determined from peak areas or the like.

BRIEF DESCRIPTION OF THE DRAWINGS (FIG. 1) is a schematic diagram of the relevant parts of an LC/MS serving as an embodiment of the present invention.

(FIG. 2) is a flowchart of the time of the creation of an analysis condition table in the LC/MS of this embodiment.

(FIG. 3) shows an example of a compound table in the LC/MS of this embodiment.

(FIG. 4) shows the state of the loop times of each of the measurement sections in the LC/MS of this embodiment.

(FIG. 5) shows an example of the analysis condition table ultimately obtained in the LC/MS of this embodiment.

(FIG. 6) shows the measurement section setting state prior to measurement section adjustment processing in the LC/MS of this embodiment.

(FIG. 7) shows the measurement section setting state during the execution of measurement section adjustment processing in the LC/MS of this embodiment.

(FIG. 8) shows the measurement section setting state after the execution of measurement section adjustment processing in the LC/MS of this embodiment.

(FIG. 9) shows an example of a typical compound table.

(FIG. 10) shows an example of a typical analysis condition table.

(FIG. 11) shows the state of the loop times of each of the measurement sections under the conditions of the analysis condition table shown in FIG. 10.

DETAILED DESCRIPTION OF THE EXEMPLARY EMBODIMENTS

A liquid chromatograph mass spectrometer (LC/MS) serving as an embodiment of the present invention will be described hereinafter with reference to the attached drawings.

FIG. 1 is a schematic diagram of the relevant parts of the LC/MS of this embodiment. The LC/MS of this embodiment comprises a liquid chromatograph (LC) part 1 for separating various compounds contained in a sample in the time direction and a mass spectrometry (MS) part 2 for performing mass spectrometry on the various separated compounds.

The LC part 1 comprises a mobile phase container 11 in which a mobile phase is stored, a liquid feeding pump 12 for aspirating the mobile phase and feeding the mobile phase at a constant flow rate, an injector 13 for injecting a sample into the mobile phase with a prescribed timing, and a column 14 for separating various compounds in the sample in the time direction.

The MS part 2 comprises an electrostatic spray 21 for electrostatically spraying an eluate containing compounds eluted from the column 14 into atmospheric air to ionize the compounds, a heating capillary 22 for guiding ions derived from the compounds in the sample into a vacuum atmosphere, ion guides 23 and 24 for converging the ions and transferring the ions to the next stage, a quadrupole mass filter 25 which only allows ions having specific mass-to-charge ratios to pass through, and a detector 26 for detecting ions passing through the quadrupole mass filter 25.

After a detection signal obtained by the detector 26 of the MS part 2 is converted to a digital value by an A/D converter not shown in the drawing, the signal is inputted into a data processing part 3. The data processing part 3 performs prescribed arithmetic processing so as to create mass spectrums or chromatograms or to execute quantitative analysis. A control part 4 respectively controls the operations of the LC part 1, the MS part 2, and the data processing part 3. The control part 4 contains an analysis condition table generation part 41 serving as a functional block characteristic to the present invention, and a storage part 5 in which a compound table or an analysis condition table is stored, an input part 6 such as a keyboard or a pointing device to be operated by an operator such as an analyst, and a display part 7 for displaying information inputted and set by the operator or analytical results are connected to the control part 4. The data processing part 3 and the control part 4 may use a personal computer configured so as to contain a CPU, memory, and the like as hardware, and the functions thereof can be realized by executing control/processing software installed in advance with the personal computer.

An example of the operation of performing quantitative analyses of known compounds contained in a sample with the LC/MS of this embodiment will be described simply hereinafter. In this case, the quadrupole mass filter 25 of the MS part 2 is driven in the SIM measurement mode so as to selectively allow the mass-to-charge ratios of ions derived from a compound to be subjected to quantitative analysis (called a target compound hereinafter) to pass through.

In a state in which the mobile phase is fed by the liquid feeding pump 12 into the column 14 at a constant flow rate, the injector 13 injects a sample into the mobile phase. The sample is introduced into the column 14 by means of the flow of the mobile phase, and various compounds in the sample are separated over time while the sample passes through the column 14. A target compound is eluted from the outlet of the column 14 in the vicinity of the point in time after a prescribed amount of time has elapsed using the sample injection time as a reference (that is, in the vicinity of the retention time of the target compound), and when the target compound reaches the electrostatic spray 21 of the MS part 2, ions derived from the compound are generated. These ions are introduced into the quadrupole mass filter 25 via the heating capillary 22, and the ion guides 23 and 24. The quadrupole mass filter 25 selectively allows only ions having specific mass-to-charge ratios derived from the target compound to pass through and the ions that pass through are detected as they reach the detector 26. The data processing part 3 creates an extracted ion chromatogram showing the relationship between the ion intensities of the specific mass-to-charge ratios and the elapsed times using data based on the detection signal obtained from the detector 26.

If the target compound is contained in the sample, a peak appears in the vicinity of the retention time of the target compound in the extracted ion chromatogram. Therefore, the data processing part 3 detects a peak derived from the target compound in the extracted ion chromatogram and calculates the peak area thereof. The content of the target compound is then found by referencing a calibration curve indicating the relationship between a predetermined peak area value and the content (concentration) of the target compound. If there are multiple compounds to be subjected to quantitative analysis, an extracted ion chromatogram for a different mass-to-charge ratio is created for each compound, and the content is similarly found from the area values by finding the respective peak areas.

In the LC/MS of this embodiment, the control part 4 controls the operations of the LC part 1, the MS part 2, and the data processing part 3 in accordance with an analysis condition table stored in an analysis condition table storage part 52 of the storage part 5. In particular, when multiple compounds contained in a sample are to be analyzed with a single sample injection, it is extremely troublesome for the actual analyst to create an analysis condition table with a manual operation, and mistakes are likely to occur. Therefore, in this LC/MS, the control part 4 is provided with an analysis condition table generation part 41 which automatically creates an analysis condition table from the compound table, and this analysis condition table generation part 41 has characteristic functions differing from the conventional automatic generation of an analysis condition table. The characteristic analysis condition table creation function executed with focus on the analysis condition table generation part 41 will be described in detail hereinafter.

Figure 2:
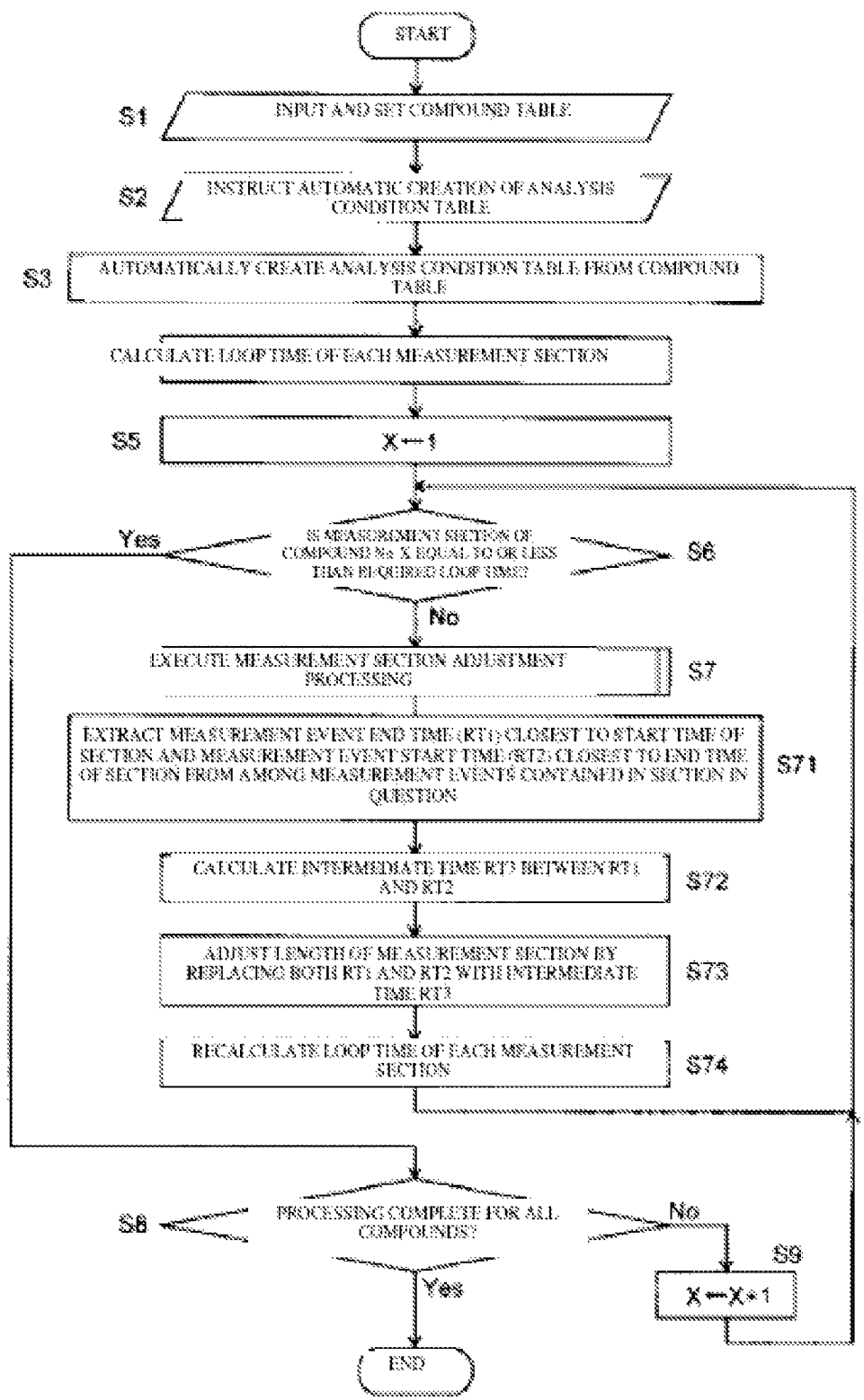
Figure 7:
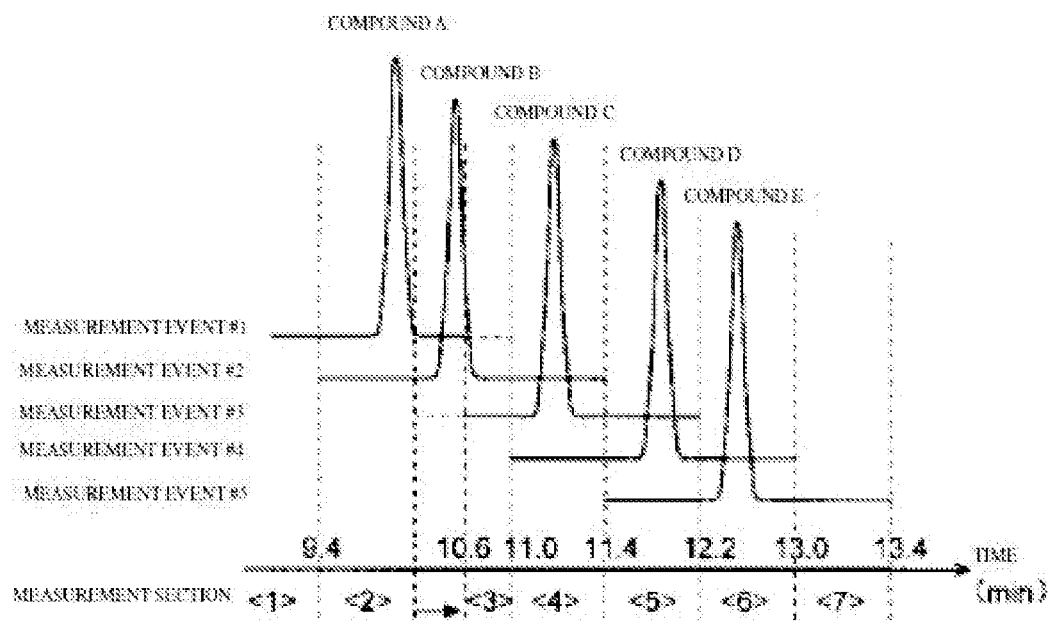
Figure 8:
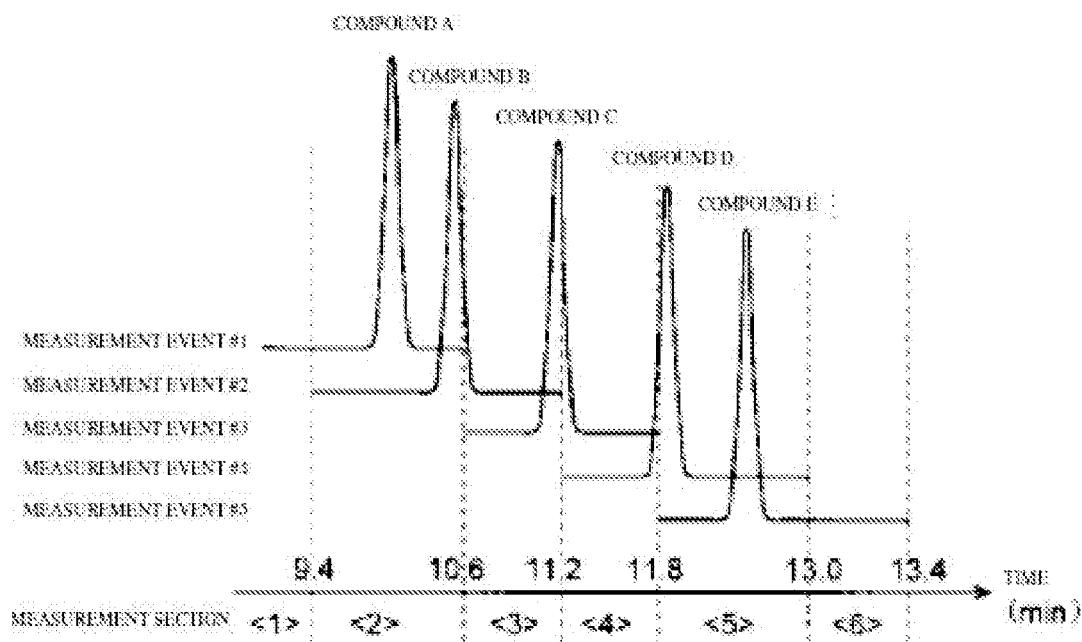

FIG. 2 is a flowchart of the time of the creation of an analysis condition table in the LC/MS of this embodiment. FIG. 3 shows an example of a compound table in the LC/MS of this embodiment. FIG. 4 shows the state of the loop times of each of the measurement sections in the LC/MS of this embodiment. FIG. 5 shows an example of the analysis condition table ultimately obtained in the LC/MS of this embodiment. FIGS. 6 to 8 show the measurement section setting state prior to measurement section adjustment processing in the LC/MS of this embodiment and the measurement section setting states during and after the execution of measurement section processing.

First, a compound table such as that shown in FIG. 3 is inputted and set by the operator from the input part 6 (step S1). The inputted and set compound table is stored in a compound table storage part 51 of the storage part 5. As in the case of the table shown in FIG. 9, this compound table describes the mass-to-charge ratio of the quantitative ion, the mass-to-charge ratio of the confirmation ion, and the like for each compound, but in the LC/MS of this embodiment, the required loop time (corresponding to the upper limit of the measurement point time interval in the invention of this application) can be further set for each compound. In this example, the required loop time is set to 200 msec for all of the compounds, but the loop time may be given values which differ appropriately for each compound. Since the loop time corresponds to the measurement point time interval for one compound, it is possible to set the required loop time to a long value for compounds for which quantitative precision is not particularly emphasized or compounds for which it is known that the half widths of the peaks in the extracted ion chromatograms are wide, for example.

When the operator instructs the execution of automatic analysis condition table creation processing from the input part 6 (step S2), the analysis condition table generation part 41 receives the instruction and automatically creates an analysis condition table based on the designated compound table (step S3). As a result, as in the conventional case, the analysis condition table shown in FIG. 10 is created from the compound table shown in FIG. 3. Conventionally, this analysis condition table is displayed on the screen of the display part 7, and the operator must correct the parameters in the analysis condition table manually as necessary. In contrast, in the LC/MS of this embodiment, the processing beginning with step S4 is performed by the analysis condition table generation part 41.

The analysis condition table generation part 41 divides the entire measurement time into a plurality of measurement sections based on the measurement start time and the measurement end time of each compound in the analysis condition table shown in FIG. 10 and calculates the loop time for each measurement section (step S4). Here, the measurement sections are set so that the measurement start time and the measurement end time of each compound form the boundaries of the measurement section. As shown in FIG. 6, the seven measurement sections <1> to <7> are set in the analysis condition table shown in FIG. 10 (here, the range earlier in time than the measurement section <1> and the range later in time than the measurement section <7> are not considered). The loop time is determined by the number of measurement events overlapping (that is, being executed in parallel simultaneously) in one measurement section. Accordingly, as shown in FIG. 4 (*a*), the loop time is 100 msec in the measurement sections <1> and <7>, and the loop time is 200 msec in the measurement sections <2> and <6>, while the loop time is 300 msec in the measurement sections <3> to <5>.

Next, a compound designation variable X is set to 1 for the purpose of initialization (step S5), and it is assessed whether the loop times of the measurement sections of the compound for which the compound number (No) is 1 are equal to or less than the required loop time that is set for the compound in question (step S6). In step S6 immediately following the execution of step S5, the compound designation variable X is 1, so it is assessed whether the respective loop times are equal to or less than the required loop time for the measurement sections of compound A, which is compound No. 1.

As shown in FIG. 6, the measurement sections of compound A at this time are the three sections <1>, <2>, and <3>, but since the loop time is 100 msec in the measurement section <1> and the loop time is 200 msec in the measurement section <2>, both loop times are less than the required loop time. On the other hand, the loop time is 300 msec in the measurement section <3>, which exceeds the required loop time. Therefore, compound A is given an assessment of No in step S6 for the measurement section <3>, and the process proceeds to step S7, where measurement section adjustment processing is executed.

In measurement section adjustment processing, the measurement event for which the measurement end time is closest to the start time of the measurement section is extracted from a plurality of measurement events overlapping in the measurement section in question (step S71). The measurement end time at this time is defined as RT1. In addition, the measurement event for which the measurement start time is closest to the end time of the measurement section is extracted from among the plurality of measurement events overlapping in the measurement section in question. The measurement start time at this time is defined as RT2. The start time of the measurement section <3> prior to the adjustment processing shown in FIG. 6 is 10.2 min, and the end time is 11.0 min. Of the three measurement events #1, #2, and #3 overlapping in this measurement section <3>, the event for which the measurement end time is closest to 10.2 min is the measurement event #1, which has a measurement end time of 11.0 min. In addition, the event for which the measurement start time is closest to 11.0 min is the measurement event #3, which has a measurement start time of 10.2 min. Therefore, in this case, RT1=11.0 min and RT2=10.2 min.

Next, the intermediate time RT3 of RT1 and RT2 is calculated (step S72). When RT1=11.0 min and RT2=10.2 min, RT3=10.6 min. The period of the measurement event #1 is then adjusted so that the measurement end time RT1 (that is, 11.0 min) of the measurement event #1 is replaced with RT3

(that is, 10.6 min), and the period of the measurement event #3 is adjusted so that the measurement start time RT2 (that is 10.2 min) of the measurement event #3 is replaced with RT3 (that is 10.6 min) (step S73). As a result, as shown in FIG. 7, the boundary line between the measurement section <2> and the measurement section <3> moves backward, and the measurement sections <2> and <3> are adjusted so as to expand and contract, respectively. If the measurement sections are changed as described above, the loop time is recalculated for each measurement section in the same manner as in step S4 (step S74), and the process returns to step S6. At this time, as shown in FIG. 4 (b), the loop time of the measurement section <3> is reduced from 300 msec to 200 msec.

When the process returns to step S6, the measurement sections of compound A at this time are <1> and <2>, but since both of the loop times of these measurement sections are less than the required loop time, the process proceeds to step S8. In step S8, it is assessed whether the processing has been completed for all of the compounds, and if there are any unprocessed compounds, the process returns to step S6 after the compound designation variable X is incremented (step S9).

Therefore, when the process returns to step S6 from steps S8 and S9 after the completion of the processing of compound A, which is compound No. 1, it is assessed whether the loop times of the measurement sections of compound B, which is compound No. 2, are equal to or less than the required loop time. If the loop times exceed the required loop time, the processing of step S7 is executed as described above. Specifically, as is clear from FIG. 7, the measurement sections of compound B are the three sections <3>, <4>, and <5>. As can be seen from FIG. 4 (b), the loop times exceed the required loop time in both of the measurement sections <4> and <5>, so the processing of step S7 (S71 to S74) is executed for each of these measurement sections. As a result, the start times or the end times of the measurement events are adjusted so that the loop times of the measurement sections <4> and <5> are equal to or less than the required loop time.

In the example of FIGS. 3 and 10, the compound numbers extend up to 5, so when the process proceeds from step S6 to S8 at the point when X=5, it is assessed that processing has been completed for all of the compounds, and the processing ends. The final measurement sections in the example described above are sections such as those shown in FIG. 8, and the loop time of each of these measurement sections at this time is as shown in FIG. 4 (c). The analysis condition table which was in the state shown in FIG. 10 when generated automatically is then ultimately modified as shown in FIG. 5 as the measurement start times and the measurement end times are sequentially corrected in accordance with the processing described above.

As described above, the analysis condition table generation part 41 corrects the analysis condition table by automatically adjusting the measurement start time and the measurement end time of each measurement event so that the loop time of each measurement section falls within the required loop time. The analysis condition table that is created and corrected in this way is saved in the analysis condition table storage part 52 of the storage part 5.

By designating the aforementioned analysis condition table saved in the analysis condition table storage part 52 from the input part 6 and executing analysis, it is possible for the operator to obtain respective extracted ion chromatograms such as those shown in FIG. 8 for compounds A to E. At this time, since the loop times in all of the measurement sections are less than the required loop time, the numbers of data points constituting the chromatogram peaks are sufficiently secured, so it is possible to sufficiently secure the precision or reproducibility of the peak shapes.

The procedure of the measurement section adjustment processing in step S7 (S71 to S74) explained in the flowchart shown in FIG. 2 is simply one example, and procedures other than that described above may also be employed.

For example, the procedure may be such that after the measurement end time RT1 and the measurement start time RT2 are found by executing the processing of step S71, the predicted retention time RTP of a compound to be observed in a measurement event ending at RT1 and the predicted retention time RTQ of a compound to be observed in a measurement event starting from RT2 are obtained in lieu of the processing of step S72, and the intermediate time between the predicted retention times RTP and RTQ may be calculated so that processing is executed using this calculated value as RT3.

In addition, the time spread of chromatogram peaks is typically dependent on the separating power of the column 14 in the LC part 1 or the mobile phase feeding conditions, and the spread of the peaks can be kept to within a certain time range as long as these satisfy certain conditions. Therefore, when it is desirable to advance the measurement end time of a given measurement event, the point in time when a prescribed amount of time (a given amount of time assuming the spread of peaks) has passed from the predicted retention time of that compound may be used as the measurement end time. The case in which it is desirable to delay the measurement start time of a measurement event is handled in the same way.

The above explanation was given based on the premise that analysis is executed after an analysis condition table is established prior to the execution of analysis, but processing differing from that of the above explanation may be employed in a configuration in which the parameters of the analysis condition table can be adaptively modified while monitoring the peaks appearing in the extracted ion chromatogram roughly in real time during the execution of analysis. That is, at a point in time when a prescribed amount of time has passed from the time when the peak top of a chromatogram peak corresponding to a target compound was obtained or at a point when the peak end point of a chromatogram peak corresponding to the target compound was detected, control should be administered to end the measurement events corresponding to that compound. When it is necessary to find the peak area in order to calculate a quantitative value, measurements must be continued until the end point of the peak, but when finding the quantitative value from the height of the peak top, it is possible to immediately end the measurement event with respect to that compound if the peak top appears.

In addition, the embodiment described above is simply a single example, and it is clear that any appropriate variations, modifications, and additions made within the scope of the gist of the present invention are included in the scope of the patent claims of this application.

For example, in the LC/MS of the embodiment described above, the MS part 2 is a single-type quadrupole mass spectrometer, but when the MS part 2 is a triple quadrupole mass spectrometer, it goes without saying that the invention of this application can be applied to SRM measurements or MRM measurements requiring the setting of analysis conditions in the same manner as in the case of SIM measurements.

EXPLANATION OF REFERENCES

1 . . . liquid chromatograph (LC) part
11 . . . mobile phase container
12 . . . liquid feeding pump
13 . . . injector 14 ... column
2 ... MS (mass spectrometry) part
21 ... electrostatic spray
22 ... heating capillary
23, 24 ... ion guides
25 ... quadrupole mass filter
26 ... detector
3 ... data processing part
4 ... control part
41 ... analysis condition table generation part
5 ... storage part
51 ... compound table storage part
52 ... analysis condition table storage part
6 ... input part
7 ... display part

What is claimed is:

1. A chromatograph mass spectrometer combining a chromatograph for separating compounds in a sample in the time direction and a mass spectrometer for separating and detecting ions derived from the compounds separated by the chromatograph in accordance with the mass-to-charge ratio, wherein said mass spectrometer executes selected ion monitoring (SIM), selection reaction monitoring (SRM), or multiple reaction monitoring (MRM) with respect to one or a plurality of specific mass-to-charge ratios in the vicinity of a chromatogram peak corresponding to a target compound, said chromatogram mass spectrometer comprising:

a) a compound table holding means which stores a compound table containing information indicating, for each compound to be measured, at least the standard predicted retention time, the mass-to-charge ratio characterizing the compound, and the upper limit of the measurement point time interval; and b) an analysis condition table creation means which, in order to perform SIM measurements, SRM measurements, or MRM measurements on compounds listed in said compound table, creates an analysis condition table containing information indicating at least the measurement time range and the mass-to-charge ratios to be measured for each compound to be measured based on the information contained in said compound table;

wherein said analysis condition table creation means includes a correction means which, after said analysis condition table creation means temporarily creates an analysis condition table based on the information contained in said compound table, corrects the analysis condition table by adjusting the start time and the end time of the measurement time range for each compound so that the measurement time interval for each compound falls within the upper limit of the measurement time interval set in said compound table.

2. The chromatograph mass spectrometer according to claim 1, wherein:

if measurement times for a plurality of specified compounds overlap in time in the analysis condition table so that the measurement point time interval exceeds said upper limit in the overlapping sections, said correction means advances the end time of a first measurement period which ends earliest among the overlapping sections and postpones the start time of a second measurement period which starts latest among the overlapping sections so as to eliminate the overlapping of the first measurement period and the second measurement period in time.

3. The chromatograph mass spectrometer according to claim 2, wherein:

said correction means finds the intermediate time between the end time of the first measurement interval and the start time of the second measurement interval, advances the end time of the first measurement interval to the intermediate time, and postpones the start time of the second measurement interval to the intermediate time.

* * * * *